United States Patent [19]
Hashimoto et al.

[11] Patent Number: 4,913,914
[45] Date of Patent: Apr. 3, 1990

[54] METHOD OF CONTROLLING THE FERMENTATION OF MOROMI MASH

[75] Inventors: Hikotaka Hashimoto; Kunio Kobayashi, both of Chiba, Japan

[73] Assignee: Kikkoman Corporation, Japan

[21] Appl. No.: 173,124

[22] Filed: Mar. 25, 1988

[30] Foreign Application Priority Data

Mar. 25, 1987 [JP] Japan ................... 62-68943

[51] Int. Cl.$^4$ .......................... A23L 1/20; A23L 1/00; A01K 43/00; G01N 33/02
[52] U.S. Cl. ...................................... 426/46; 426/231
[58] Field of Search ...................... 426/231, 46, 18, 44

[56] References Cited

U.S. PATENT DOCUMENTS 4,083,690  4/1978  Inoue ................................. 426/231
4,751,185  6/1988  Ono et al. ......................... 426/231

Primary Examiner—Marianne Cintins
Attorney, Agent, or Firm—Scherlacher, Mok & Roth

[57] ABSTRACT

A fast, accurate and low cost method of controlling the fermentation of moromi mash includes the steps of automatically sampling a portion of the mash, automatically and simultaneously analyzing the concentrations of at least two ingredients in the sampled portion, calculating an amount to be added of at least one controlling element to adjust the concentrations of the two ingredients to target values and adding the calculated amount of the controlling element to the moromi mash, an infrared analyzer is used to automatically and simultaneously determine the concentrations of key ingredients from a single sample.

5 Claims, 4 Drawing Sheets

METHOD OF CONTROLLING THE FERMENTATION OF MOROMI MASH

BACKGROUND OF THE INVENTION

1. Field of the Invention:

The present invention relates to a method of and an apparatus for controlling fermentation, and more particularly to a method of and an apparatus for controlling the fermentation of moromi- mash.

2. Description of the Relevant Art:

During fermentation of moromi mash in the process of manufacturing soy sauce or shoyu, soybean protein and wheat starch are progressively converted to amino acid and glucose, respectively, by koji-mold. A portion of the glucose is then progressively converted to alcohol and lactic acid by yeast and lactic acid bacteria, respectively. In the moromi mash fermentation, therefore, amino acid and glucose are produced from soybean protein and wheat starch, respectively, and alcohol and lactic acid are produced from the glucose. After the fermentation, ripened moromi mash is pressed to produce raw soy sauce. The quality of raw soy sauce is greatly affected by the balancing of the amounts produced of glucose, lactic acid, and alcohol. In order to adjust the concentrations of these ingredients to desired levels, the moromi mash or its liquid is extracted periodically during the fermentation process to analyze the ingredients. Based on analytic results, yeast and lactic acid bacteria are added to the moromi mash, and aeration and temperature of the entire moromi mash are adjusted.

Nitrogen, which is indicative of the concentration of amino acid, is analyzed by the Kheldahl method, and alcohol is analyzed by gas chromatography. Glucose and lactic acid are analyzed mainly by the enzymatic method. Glutamic acid, which is an amino acid and governs the flavor of soy sauce, is also analyzed mainly by the enzymatic method. These analytic processes have heretofore been effected manually over long periods of time using independent analyzing devices. The analysis of nitrogen, particularly, has required several ours. Therefore, a prolonged period of time is needed to carry out the analytic processes, add yeast and lactic acid bacteria based on analytic results, aerate the moromi mash, and adjust the temperature of the moromi mash. Since the ingredient analysis and the subsequent processing steps are effected at periodic intervals, it has been difficult to increase the efficiency of and automate the process of fermenting moromi mash. Therefore, an efficient and automated device for fermenting moromi mash has not been available in the art.

The present invention has been made in an effort to solve the above problems with the conventional method and apparatus for fermenting moromi mash.

SUMMARY OF THE INVENTION

It is an object of the present invention to provide a method of controlling the fermentaion of moromi mash efficiently on an automated basis by efficiently and automatically analyzing ingredients of the moromi mash and effecting subsequent processing steps.

Another object of the present invention is to provide an apparatus for controlling the fermentaion of moromi mash efficiently on an automated basis with an efficient and automatic device for analyzing ingredients of the moromi mash and adding additives to the moromi mash periodically.

To achieve the above objects, there is provided a method of controlling the fermentation of moromi mash, comprising the steps of sampling a portion of a prescribed amount of moromi mash, simultaneously analyzing the concentrations of at least two ingredients of the sampled portion of the moromi mash, calculating the amount to be added of at least one controlling element in order to adjust the concentrations of the at least two ingredients to target values according to analytic results, adding the calculated amount of the at least one controlling element to the prescribed amount of moromi mash, and periodically repeating the sampling, analyzing, calculating, and adding steps throuogut a fermentation period of the moromi mash.

There is also provided an apparatus for controlling the fermentation of moromi mash, comprising at least one storage tank for storing a prescribed amount of moromi mash, a sampling mechanism for sampling a portion of the prescribed amount of moromi mash, an automatic multiple analyzer for receiving the portion of the prescribed amount of moromi mash from the sampling mechanism and simultaneously analyzing the concentrations of at least two ingredients of the sampled portion of the moromi mash, at least one control tank operatively communicating with the storage tank for storing at least one controlling element and supplying the controlling element to the moromi mash in the storage tank, control valve means operatively coupled between the control tank and the storage tank for controlling the amount of the controlling element to be supplied to the moromi mash in the storage tank, and control means operatively connected to the automatic multiple analyzer and the control valve means for periodically operating the sampling mechanism and the automatic multiple analyzer to enable the automatic multiple analyzer to analyze the at least two ingredients of the portion of moromi mash during a fermentation period of the moromi mash, the control means including means for selectively opening and closing the control valve means according to analytic results from the automatic multiple analyzer thereby to add the controlling element to the moromi mash in the storage tank to adjust the concentrations of the at least two ingredients of the prescribed amount of moromi mash to target values.

The above and further objects, details and advantages of the present invention will become apparent from the following detailed description of preferred embodiments thereof, when read in conjunction with the accompanying drawings.

DETAILED DESCRIPTION OF THE PREFERRED EMBODIMENTS

Figure 1:
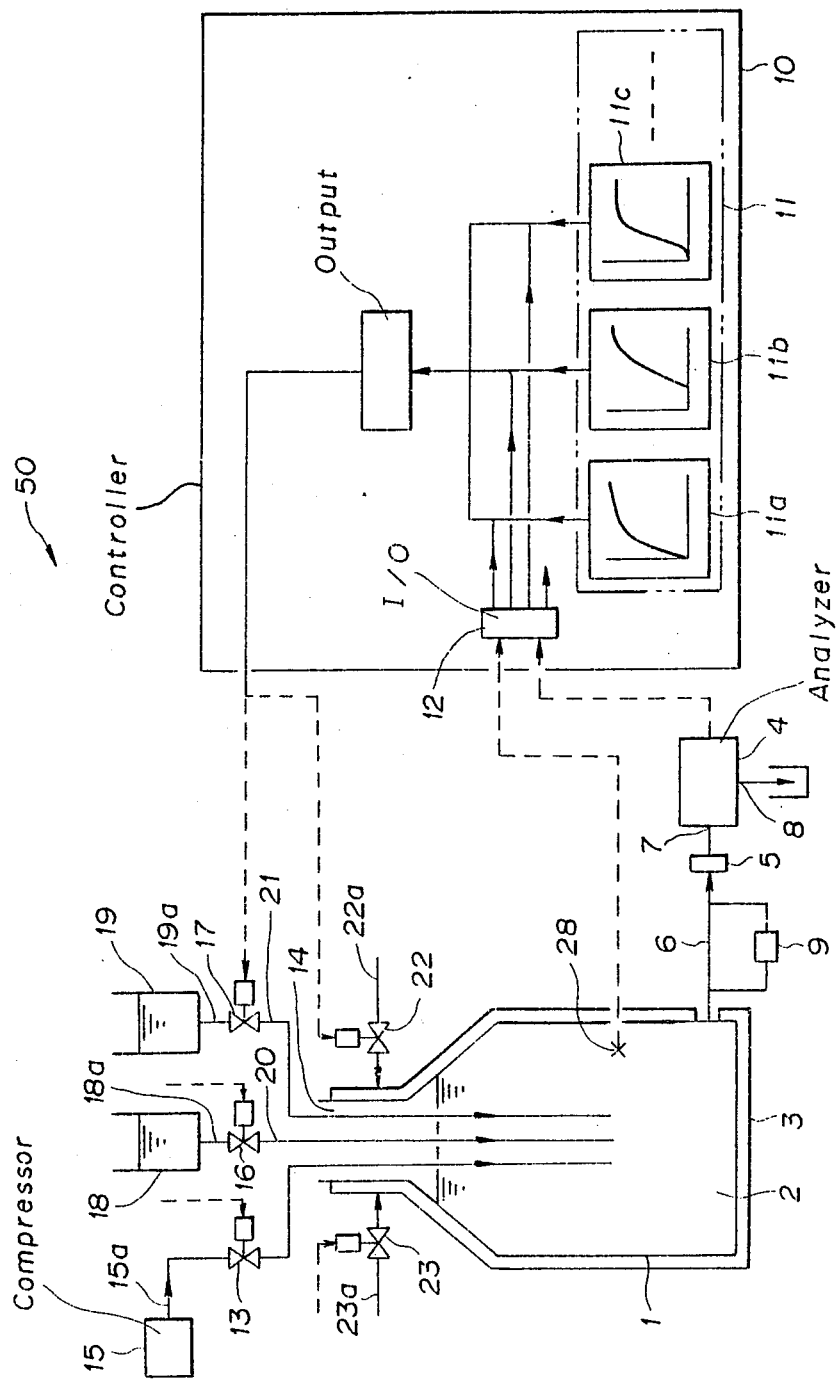
FIG. 1 is a diagram of an apparatus for fermenting moromi mash, which is used to carry out a control method according to a first embodiment of the present invention.

As shown in FIG. 1, an apparatus, generally designated by the reference numeral 50, for fermenting moromi mash according to a first embodiment of the present invention, includes a fermentation tank 1 for storing a predetermined amount of moromi mash 2, the tank 1 being covered with a temperature-adjusting jacket 3. Cooling water and heated steam are exclusively supplied to the tank 1 through a cooling valve 23 and a heat source valve 22 (described later on), respectively. A portion of the liquid of the moromi mash 2 in the tank 1 is led to a sample column 7 of an automatic multiple analyzer 4 through a pump 5 and a pipe 6. The automatic multiple analyzer 4 has a discharge port 8 for discharging analyzed moromi mash. A homogenizer 9 coupled parallel to the pipe 6 is actuated when particles are present in the moromi mash in the pipe 6. A filter unit may be employed in place of the homogenizer 9 to supply filtered moromi mash to the analyzer 4. The apparatus 50 also has a controller 10, described later.

A procedure for analyzing the moromi mash with the automatic multiple analyzer 4 will now be described with reference to FIG. 2.

Figure 2:
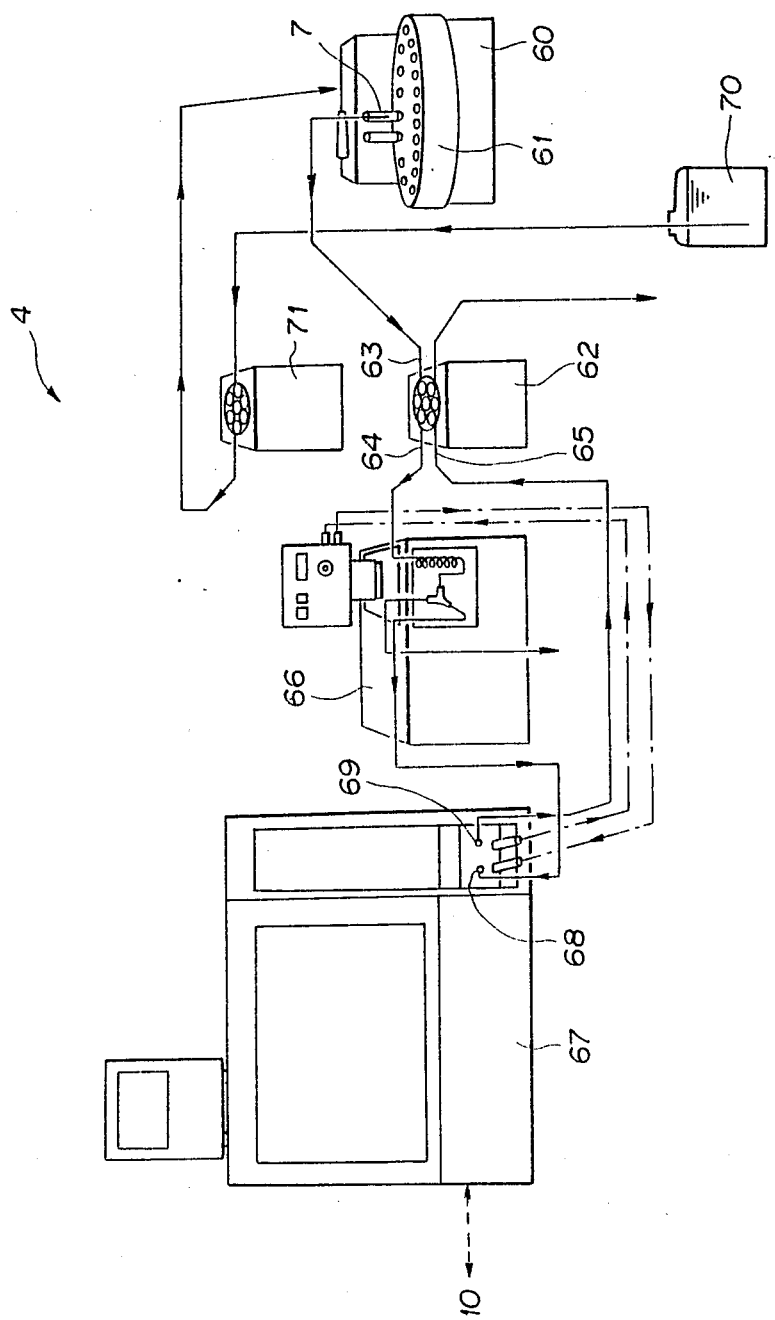
FIG. 2 is a view of a near-infrared analyzer used as an automatic multiple analyzer in the fermenting apparatus shown in FIG. 1.

FIG. 2 shows a specific arrangement of the automatic multiple analyzer 4. The analyzer 4 includes a sampler 60 (which may be Sampler Type 4 manufactured by Technicon) having a turntable 61 supporting thereon a plurality of columns 7 in the shape of test tubes. The turntable 61 rotates with a prescribed one of the columns 6 being in an upwardly erected position. When the turntable 61 reaches a given angular position, a sample in the column 7, i.e., a moromi mash liquid is fed to an inlet port 63 of a peristaltic pump 62. The peristaltic pump 62 has an outlet port 64 connected to a sample supply port 68 of a near-infrared analyzer unit 67 through a cooling unit 66 for keeping the sample from the column 7 at a low temperature. The near-infrared analyzer unit 67 may be Infra Alyzer 400LR manufactured by Technicon. The analyzer unit 67 has a sample discharge port 69 coupled to another inlet port 65 of the peristaltic pump 62 for discharging the analyzed sample. The sample discharge port 69 and the inlet port 65 are connected to the disharge port 8. A washing solution 70 is supplied, alternately with the sample, to the column 7 by another peristaltic pump 71. Since the sample and the washing solution are alternately supplied from the column 7 to the analyzer unit 67, therefore, samples will not be mixed with each other.

The sample or moromi mash liquid may be supplied directly to the sample supply port 68 of the near-infrared analyzer unit 67 by the pump 5.

As shown in FIG. 1, the apparatus 50 also includes a compressor 15, a yeast tank 18, and a lactic acid bacteria tank 19 which are held in communication with the tank 1 through respective pipes 15a, 20, 21 extending through an upper opening 14 of the tank 1. The lines 15a, 20, 21 have an air valve 13 and control valves 16, 17, respectively, above the upper opening 14. While the valves 16, 17, 13 are being opened under the control of the controller 10, yeast and lactic acid bacteria are added to the moromi mash 2, and the moromi mash 2 is aerated. The jacket 3 is coupled to a heating medium source (not shown) of hot air, heated steam, or the like through a line 22a, and also to a cooling medium source (not shown) of cooling water or the like through a line 23a. The lines 22a, 23a have the heat source valve 22 and the cooling valve 23, respectively, which are controlled by the controller 10. When the air valve 13 is opened, fresh air is introduced into the moromi mash 2 under pressure to promote propagation of existing microorganisms such as yeast, lactic acid bacteria, and the like, and at the same time to aerate the moromi mash 2 to mix the same. Therefore, yeast and/or lactic acid bacteria which may have newly been added are uniformly distributed in the moromi mash 2, and the heat of the cooling medium or the heating medium introduced into the jacket 3 is uniformly transferred to the moromi mash 2. The yeast, the lactic acid, the heat, and the aeration serve as controlling elements.

The controller 10 comprises a microcomputer having an interface 12, a CPU, a RAM, a ROM, and other circuits (not shown). Signals from the analyzer 4 and a temperature sensor 28 in the tank 1 are applied to the interface 12 of the controller 10. The ROM in the controller 10 stores data 11 indicating the ideal relationships between time and the concentrations of nitrogen, alcohol (ethanol), lactic acid, glutamic acid, glucose, etc., in the moromi mash 2 throughout the period of fermentation. The data 11 comprise graph data 11a, 11b, 11c, with respect to the ingredients such as nitrogen, alcohol, lactic acid, and others. The data 11 also include graph data (not shown) representative of the ideal relationship between time and pH values of the moromi mash 2. The controller 10 periodically compares the values of output signals from the analyzer 4 with the data 11 and opens the control valves 16, 17 for required times in view of the results of the comparison. The output signals from the analyzer 4 include serial data signals indicative of the concentrations and pH values of the ingredients of the sample moromi mash liquid. These data signals are successively compared with the graph data 11a, 11b, 11c, At the same time, the controller 10 opens the air valve 13 while opening the heat source valve 22 or the cooling valve 23 based on a detected signal from the temperature sensor 28 for thereby adjusting the temperature of the entire moromi mash 2 to a required temperature, thus assisting the concentrations of the ingredients of the moromi mash 2 in approaching the ideal values.

The controller 10 may be another circuit having the same functions as those of a microcomputer.

During the fermentation process of the moromi mash 2, the controller 10 periodically actuates the pump 5 to feed the moromi mash liquid to the analyzer 4 and receives analytic results by way of output signals from the analyzer 4. The controller 10 further compares the output signals from the analyzer 4 with the data 11, and opens the valves 16, 17 for periods of time dependent on the results of the comparison. Thereafter, the controller 10 opens the air valve 13 while opening the heat source valve 22 or the cooling valve 23 to adjust the temperature of the entire moromi mash 2 to a required temperature. Such aeration is also effective in uniformly distributing yeast and lactic acid bacteria that may have been added throughout the moromi mash 2. As an example, the fermentation period may be about one year, and the controller 10 may analyze and adjust the ingredients of the moromi mash 2 once every few days.

Analysis of the moromi mash liquid with the near-infrared analyzer 4 will hereinafter be compared with a conventional analytic procedure.

The near-infrared analyzer 4 or the near-infrared analyzer unit 67 applies near-infrared radiation to the sample, and checks the reflectivity or transmittance of the radiation for thereby analyzing a certain ingredient of the sample. More specifically, for increased accuracy of analytic values, the reflectivity of the infrared radiation is measured at several wavelengths in the near-infrared range, and various ingredient values of the moromi mash liquid are calculated on the basis of the following regression equations and regression coefficients, where ABS(N) indicates the absorbance, with the unit in each equation being W/V (weight/volume) %:

Regression equations:

$$\text{Nitrogen} = 0.696 - 35.83 \cdot ABS(4) + 143.5 \cdot ABS(7) - 86.60 \cdot ABS(9) - 165.0 \cdot ABS(13) + 28.98 \cdot ABS(20) + 122.2 \cdot ABS(20);$$

$$\text{Alcohol} = -21.96 - 310.9 \cdot ABS(2) + 380.7 \cdot ABS(4) - 250.5 \cdot ABS(6) + 115.2 \cdot ABS(7) + 71.75 \cdot ABS(19) + 71.20 \cdot ABS(20);$$

$$\text{Lactic acid} = 22.80 + 489.0 \cdot ABS(6) - 803.0 \cdot ABS(7) + 291.4 \cdot ABS(9) + 936.1 \cdot ABS(12) - 1270 \cdot ABS(13) + 293.2 \cdot ABS(20);$$

$$\text{Glutamic acid} = -5.501 - 157.1 \cdot ABS(3) + 129.1 \cdot ABS(4) - 65.23 \cdot ABS(5) + 288.9 \cdot ABS(7) - 267.3 \cdot ABS(10) + 98.46 \cdot ABS(14);$$

$$\text{Glucose} = -7.981 - 2781.0 \cdot ABS(8) - 81.17 \cdot ABS(11) - 1519.3 \cdot ABS(12) + 4680.1 \cdot ABS(13) - 141.6 \cdot ABS(19)$$

Regression coefficients:
Nitrogen: 0.9948;
Alcohol: 0.9940;
Lactic acid: 0.8814;
Glutamic acid: 0.9145;
Glucose: 0.8641.

The times required to analyze (a) nitrogen, (b) alcohol, (c) lactic acid, (d) glutamic acid, and (e) glucose in a sample and analyzed values of these ingredients are given for comparison in the following tables 1 and 2 with respect to the inventive process effected by the near-infrared analyzer 4 and conventional processes.

In the table 1, the times are expressed in minutes. The conventional processes used were the Kheldahl method for nitrogen, the gas chromatography for alcohol, and the enzymatic method for lactic acid, glutamic acid, and glucose. The rightmost column of the table 1 indicates total times each required to analyze one sample.

TABLE 1

|  | (a) | (b) | (c) | (d) | (e) | Total time |
|---|---|---|---|---|---|---|
| Inventive process | (3) | (3) | (3) | (3) | (3) | 3 |
| Conventional processes | 120 | 15 | 30 | 30 | 30 | 225 |

TABLE 2

|  | (a) | (b) | (c) | (d) | (e) |
|---|---|---|---|---|---|
| Inventive process | 1.843 | 1.84 | 1.38 | 1.49 | 2.0 |
| Conventional process | 1.849 | 1.83 | 1.34 | 1.47 | 1.9 |

(Unit: % (W/V))

According to the process of the present invention, as can be understood from the above tables 1 and 2, the moromi mash ingredients can be analyzed with the same accuracy as that of the conventional processes in periods of time which are much shorter than those of the conventional processes.

Figure 3:
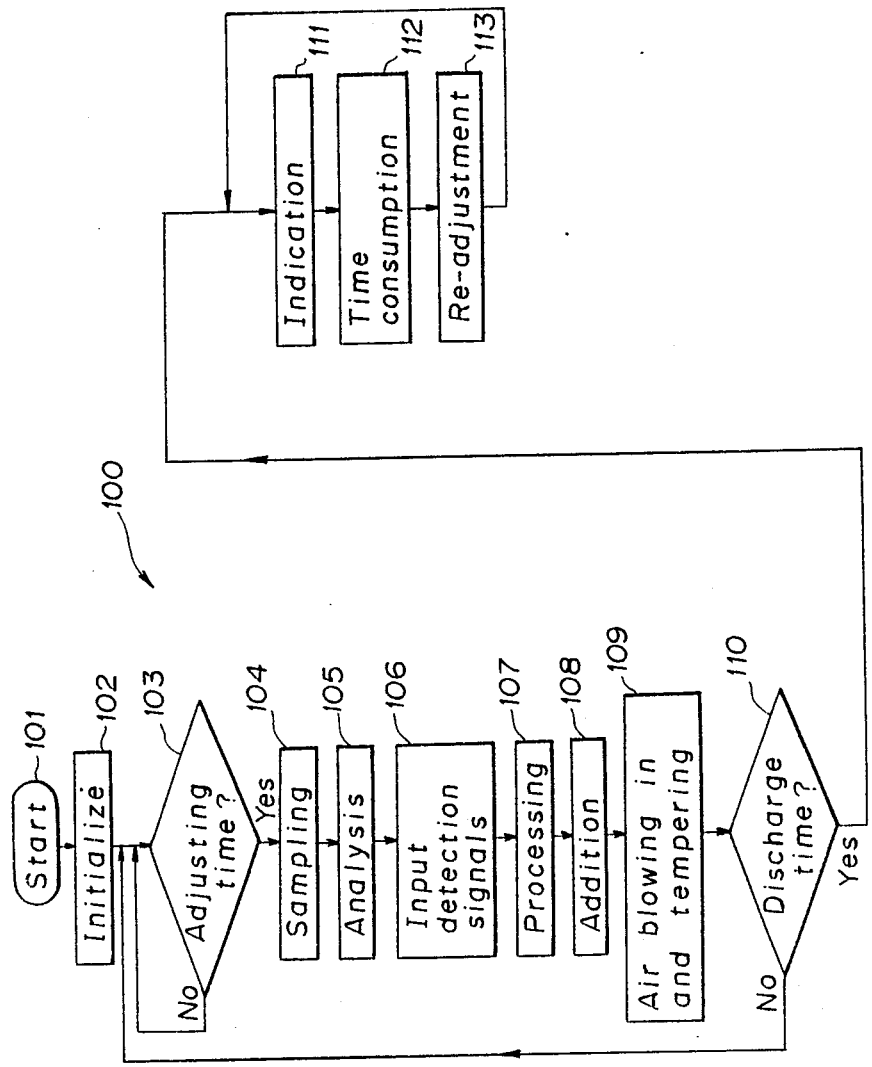
FIG. 3 is a flowchart of a processing sequence carried out by a controller in the apparatus of FIG. 1.

FIG. 3 shows a schematic flowchart 100 to be executed by the controller 10 of the apparatus 50.

When the apparatus 50 is started after a prescribed amount of moromi mash 2 has been introduced into the tank 1, the controller 10 is energized to start the processing from a step 101.

The circuits and variables in the controller 10 are initialized in a step 102. Since the fermentation period of the moromi mash 2 is long, i.e., about one year, a software calender which is updated with time in relation to an internal timer is reset.

A next step 103 ascertains whether time has come to adjust the fermentation of the moromi mash 2 with reference to the software calender. If not, then control repeats the step 103 for idling. If yes, then control goes to a next step 104. Dependent on the decision made by the step 103, the processing after the step 104 is effected once every few days.

In a step 104, the pump 5 is operated to enable the near-infrared analyzer 4 to sample a portion of the liquid of the moromi mash 2 in the tank 1. In a next step 105, the concentrations and pH values of the ingredients of the moromi mash liquid are analyzed by the near-infrared analyzer 4. During the step 105, the controller 10 is kept in a standby condition while consuming time.

In a step 106, output signals indicative of analytic results are sent from the analyzer 4 to the controller 10, and an output signal from the temperature sensor 28 is also applied to the controller 10.

In a step 107, the controller 10 compares the values of the output signals from the analyzer 4 with the graph data 11a, 11b, 11c, ... - stored in the controller 10 in view of the detected signal from the temperature sensor 28 and with reference to the software calender. Then, the controller 10 determines the amounts of yeast and lactic acid bacteria to be added to the moromi mash 2 and the amount of air to be introduced into the moromi mash 2, and also determines the temperature to which the jacket 3 is to be adjusted.

In a step 108, the control valves 16, 17 are opened by the controller 10 for periods of time according to the amounts which are determined in the step 107. The required amounts of yeast and/or lactic acid bacteria are now added to the moromi mash 2.

The air valve 13 is then opened for a required period of time in a step 109 to deliver fresh air under pressure into the moromi mash 2. During this time, the heat source valve 22 or the cooling valve 23 remains continuously open to adjust the temperature of the entire moromi mash 2 to a required temperature. Such aeration is effective in uniformly distributing yeast and/or lactic acid bacteria throughout the moromi mash 2. The temperature of the moromi mash 2 is confirmed by the detected signal from the temperature sensor 28. The processing of the step 109 is carried out in view of the software calender.

A next step 110 ascertains whether a prescribed fermentation period, e.g., one year, has elapsed or not with reference to the software calender. If yes, then control proceeds to a step 111, and if not, then control goes back to the step 103 to continue idling until a next moromi mash adjusting time comes.

In the step 111, an indicator (not shown) on a control panel (not shown) of the controller 10 is energized to indicate that the given fermentation period has elapsed.

The time period of seven to ten days is then allowed to elapse in a step 112.

In a step 113, the moromi mash 2 is adjusted in the same manner as that which is carried out in the steps 104 through 109. Thereafter, control goes back to the step 111 again. Therefore, the steps 111 through 113 are repeated until the ripened moromi mash 2 is delivered to a non-illustrated pressing process by the operator or supervisor.

The step 113 may be omitted from the above sequence. The steps 111 through 113 may be replaced with a step of automatically delivering the ripened moromi mash 2 to a next process. Moreover, the yeast tank 18 and the lactic acid bacteria tank 19 may be held in communication with the tank 1 through pumps controlled by the controller 10, rather than through the control valves 16, 17.

With the present invention, as described above, the ingredients of the moromi mash 2 in the tank 1 are automatically analyzed in a short interval of time by the near-infrared analyzer 4, and the ingredients and the temperature of the moromi mash 2 are adjusted as required. Such an adjusting process is automatically effected periodically throughout the moromi mash fermentation period. Therefore, the process of analyzing the ingredients and any subsequent process can be carried out efficiently on an automated basis, with the result that the method of controlling the fermentation of moromi mash is rendered efficient and automated. Stated otherwise, the equipment employed to carry out the process of analyzing the ingredients and any subsequent process is also rendered efficient and automated, and so is the apparatus 50 for controlling the fermentation of moromi mash.

Materials or products that can be analyzed by the automatic multiple analyzer 4 are not limited to the moromi mash 2. Almost all other varieties of soy sauce such for example as dark-colored soy sauce (known as "koikuchi shoyu"), light-colored soy sauce (known as "usukuchi shoyu"), supernatant soy sauce (known as "tamari shoyu"), and clear soy sauce (known as "shiro shoyu") may also be analyzed by the automatic multiple analyzer 4. The ingredients to be analyzed depend on the type of soy sauce. For dark-colored soy sauce, for instance, nitrogen, alcohol, lactic acid, glutamic acid, and glucose are analyzed.

Where each of a plurality of fermentation tanks is held in communication with a compressor, a yeast tank, and a lactic acid bacteria tank through control valves and a portion of moromi mash is sampled from each of the fermentation tanks into a near-infrared analyzer, the plural fermentation tanks can be controlled by the single near-infrared analyzer and a single controller.

Figure 4:
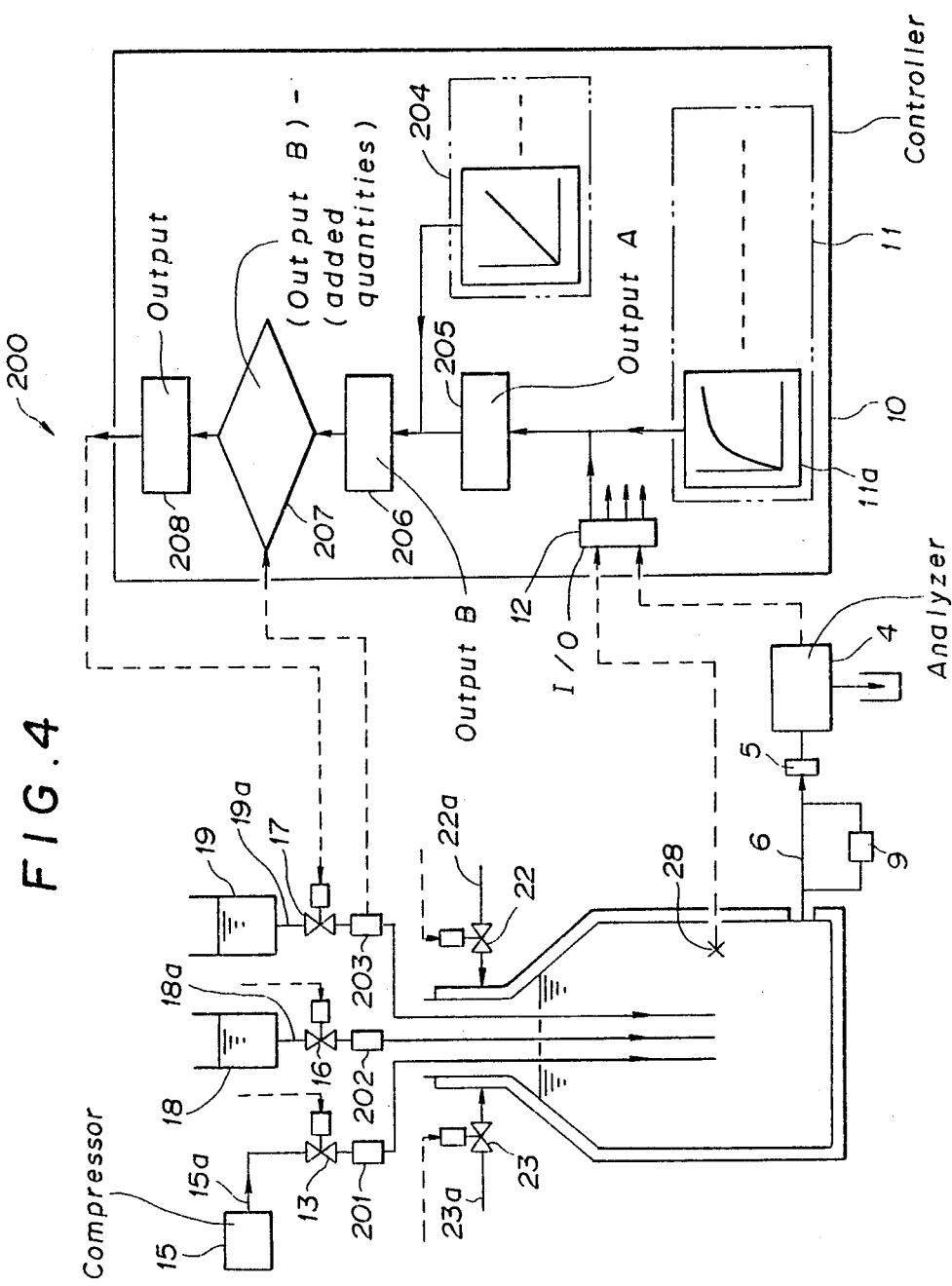
FIG. 4 is a diagram of an apparatus for fermenting moromi mash, which is used to carry out a control method according to a second embodiment of the present invention.

FIG. 4 shows an apparatus 200 for fermenting moromi mash according to a second embodiment of the present invention. The apparatus 200 is basically identical in construction to the apparatus 50 shown in FIG. 1. Those parts of the apparatus 200 which are identical to those of the apparatus 50 are denoted by identical reference numerals, and will not be described in detail.

The apparatus 200 additionally has flow sensors 201, 202, 203 disposed in the lines 15a, 18a, 19a of the compressor 15, the yeast tank 18, and the lactic acid bacteria tank 19 and positioned downstream of the valves 13, 16, 17, respectively.

The controller 10 additionally stores in its ROM graph data 204 indicative of the amounts to be added of or the preset values for controlling elements (air, yeast, lactic acid bacteria, and heat) dependent on the differences between the output signals from the analyzer 4 and the temperature sensor 28 and the stored data 11. Output signals B to be applied to the valves 13, 16, 17 and 22 or 23 are determined based on an output signal A and the graph data 204. Signals from the flow sensors 201, 202, 203 are fed back to the controller 10 until the differences between the output signals B and the supplied total amounts are eliminated.

With the flow sensors 201, 202, 203, the apparatus 200 can control the amount of air to be introduced into the moromi mash, the amount of yeast to be added to the moromi mash, and the amount of lactic acid bacteria to be added to the moromi mash, more precisely than the apparatus 50.

Although there have been described what are presently considered to be the preferred embodiments of the present invention, it will be understood that the invention may be embodied in other specific forms without departing rom the spirit or essential characteristics thereof. The present embodiments are therefore to be considered in all aspects as illustrative, and not restrictive. The scope of the invention is indicated by the appended claims rather than by the foregoing description.

We claim:

1. A method of controlling the fermentation of moromi mash, comprising the steps of:
   automatically sampling a portion of a prescribed amount of moromi mash;
   automatically and simultaneously analyzing the concentrations of at least two ingredients of the sampled portion of the moromi mash with a near infrared automatic multiple analyzer;
   calculating an amount to be added of at least one controlling element in order to adjust the concentrations of said at least two ingredients to target values according to analytic results;
   adding the calculated amount of said at least one controlling element to said prescribed amount of moromi mash; and
   periodically repeating said sampling, analyzing, calculating, and adding steps throughout a fermentation period of the moromi mash.

2. A method according to claim 1, wherein said concentrations are analyzed by simultaneously analyzing the concentrations of nitrogen, alcohol, lactic acid, glutamic acid, and glucose, and the pH value of the moromi mash.

3. A method according to claim 1, wherein the calculating step includes the steps of calculating the amount of yeast, the amount of lactic acid bacteria, and the amount of air to be added to the moromi mash, and calculating a temperature at which the moromi mash is to be maintained and wherein the method further includes the step of automatically controlling the temperature of the moromi mash to maintain the calculated temperature.

4. A method according to claim 1 wherein said automatic and simultaneous analyzing step includes the steps of determining at least one light responsive characteristic of a single portion of said automatically sampled mash and determining concentrations of said at least two ingredients in response to the determined at least one light responsive characteristic.

5. A method of controlling the fermentation of moromi mash, comprising the steps of:
   automatically sampling a portion of a prescribed amount of moromi mash with a near infrared automatic multiple analyzer;
   automatically and simultaneously analyzing the concentrations of at least two ingredients of the sampled portion of the moromi mash;
   calculating the amount to be added of at least one controlling element in order to adjust the concentrations of said at least two ingredients to target values according to analytic results; and
   adding the calculated amount of said at least one controlling element to said prescribed amount of moromi mash.

* * * * *

UNITED STATES PATENT AND TRADEMARK OFFICE
CERTIFICATE OF CORRECTION

PATENT NO. : 4,913,914

DATED : April 3, 1990

INVENTOR(S) : Hikotaka Hashimoto et al.

It is certified that error appears in the above-identified patent and that said Letters Patent is hereby corrected as shown below:

Column 1, line 43, "ours" should read --hours--.

Column 3, line 45, "disharge" should read --discharge--.

Column 5, line 13, "0.696" should read --0.796--.

Column 5, line 15, "86.60" should read --87.60--.

Column 8, line 37, "rom" should read --from--.

Signed and Sealed this

Twenty-first Day of April, 1992

Attest:

HARRY F. MANBECK, JR.

*Attesting Officer*     *Commissioner of Patents and Trademarks*